United States Patent [19]

Daniels et al.

[11] 3,949,073

[45] Apr. 6, 1976

[54] PROCESS FOR AUGMENTING CONNECTIVE MAMMALIAN TISSUE WITH IN SITU POLYMERIZABLE NATIVE COLLAGEN SOLUTION

[75] Inventors: John R. Daniels, Menlo Park; Terry R. Knapp, Santa Clara, both of Calif.

[73] Assignee: The Board of Trustees of Leland Stanford Junior University, Stanford, Calif.

[22] Filed: Nov. 18, 1974

[21] Appl. No.: 524,672

[52] U.S. Cl. .................................. 424/177; 424/359
[51] Int. Cl.² .................... A61K 37/00; A01N 9/00
[58] Field of Search .............................. 424/177, 89

[56] References Cited
UNITED STATES PATENTS
3,469,003   9/1969   Hardy .................................. 424/89

OTHER PUBLICATIONS

Shoshan et al.: Chem. Abstr. 74: 30657q (1971).
Rouveix: Chem. Abstr. 73: 133993e (1970).
Bedacht: Chem. Abstr. 74: 109758q (1971).

*Primary Examiner*—Lewis Gotts
*Assistant Examiner*—Reginald J. Suyat
*Attorney, Agent, or Firm*—Thomas E. Ciotti

[57] ABSTRACT

A method for augmenting hard or soft connective tissue, such as skin, tendon, cartilage, bone or interstitium, in a living mammal comprising implanting a proteolytic enzyme-solubilized, purified, native, in situ polymerizable collagen solution into the mammal at the augmentation site. The solution polymerizes at the site into a stable, non-reactive fibrous mass of tissue which is rapidly colonized by host cells and vascularized.

21 Claims, No Drawings

PROCESS FOR AUGMENTING CONNECTIVE MAMMALIAN TISSUE WITH IN SITU POLYMERIZABLE NATIVE COLLAGEN SOLUTION

BACKGROUND OF THE INVENTION

1. Field of the Invention

This invention is a method of augmenting or replacing connective tissue in a living mammal by implanting a solution of a natural tissue material which polymerizes upon implantation into a fibrous mass of tissue which is non-reactive, stable, resistant to secondary infection and has the potential for vascularization. Specifically, the invention resides in the use of a solution of solubilized, purified, native, in situ polymerizable collagen as the material which is implanted.

2. Brief Description of the Prior Art

Collagen is a natural material which serves as supporting tissue in many living systems. It is a principal component of skin, tendon, cartilage, bone and interstitium.

The molecular structure of collagen has been studied and documented. Collagen is characterized as a fibrous protein made up of helixes of three polypeptide chains having biologically important end regions. Collagen may be modified by treatment with proteolytic enzymes to solubilize it and lower its antigenicity[1]. It is reported that after such treatment collagen fibers tend to precipitate with increasing pH, increasing ionic strengh and increasing temperature.

[1] Gross, J., Highberger, J.H., and Schmitt, F.O., *Proc. Nat. Acad. Sci.* (US) 40:679, 1954.

Many uses of enzyme-solubilized collagen (ESC) as a biomaterial have been investigated or suggested[2,3,4]. For instance collagen gel formed by irradiating or ascorbic acid-treating ESC to prevent fiber precipitation has been used as a vitreous replacement in the eye. Also films of irradiation-crosslinked ESC have been used as corneal replacements, dialysis membranes, heart valve prostheses, vessel prostheses, burn coverings and surgical hemostasis (as a film or powder).

[2] "Collagen as a Biomaterial", Rubin, A. L. and Stenzel, K. H., Departments of Surgery and Biochemistry, Cornell University Medical College (New York).
[3] "Collagen: Medical and Surgical Applications", Rubin, A. L., Miyata, T., and Stenzel, K. H., Departments of Surgery and Biochemistry, New York Hospital-Cornell Medical Center (New York).
[4] "Medical and Surgical Applications of Collagen", Chvapil, M., Kronenthal, R., and van Winkle, W., *International Review of Connective Tissue Research*, Vol 6, pp 1–61, 1973.

Collagen has not been used previously to augment soft tissue. Prior soft tissue augmentations have involved autografts and homografts of bone, cartilage or dermis, insertion of alloplastic implants, or injection of alloplastic materials such as liquid silicone. Bone and cartilage may fill a soft tissue defect, but unless the depressed area is due to a deficiency of underlying bony framework, the lack of pliability in the augmented area will be unsatisfactory. The surgical technique of inserting bone, cartilage or dermis often involves wide undermining of soft tissue and the creation of a substantial, and sometimes additional, recipient site scar. There is also a tendency for such grafts to undergo resorption which often cannot be predicted accurately. Moreover, fine contouring of multiple small areas is often extremely difficult with such grafts. The donor sites for obtaining bone and cartilage autografts are rather limited and a noticeable scar is often created.

The donor site problems are not existent with the use of homograft material. The homograft dermis is unsuitable because it is always rejected. Rejection may be less of a problem with bone and cartilage homografts, but is unpredictable[5].

[5] The *Transplantation of Tissues*, Peer, L., Williams & Wilkins Co, Baltimore, 1959. 1959.

Solid silicone implants require that the recipient site be undermined, result in a scar at the insertion site, have a significant tendency to drift, cause seromas, become surrounded by hard fibrous tissue and occasionally become infected or erode through the overlying soft tissue. Some of these problems are shared by the injectable silicone liquids.

SUMMARY OF THE INVENTION

The invention resides in the discovery that solubilized collagen is a readily available, biologically acceptable material which may be implanted as a solution and which, upon implantation, condenses at the implantation site into non-reactive, stable tissue which is rapidly colonized by host cells and vascularized. Specifically the invention is a method of augmenting connective tissue in a living mammal comprising implanting or applying a solution of solubilized, purified, native, in situ polymerizable collagen into or onto the mammal, as the case may be, at the augmentation site which polymerizes at the site into fibrous tissue. As used in the claims the term "administering" includes the acts of implanting and applying the solution.

Since the method employs collagen in a solution implantation may be effected by conventional injection techniques rather than surgical implantation. Thus the method avoids the undermining of body tissues and scarring associated with solid alloplastic implants. It may also be used for fine contouring small, irregular tissue defects. More importantly once the material is implanted it polymerizes into fibrous tissue possessing all the attributes of an ideal prosthesis, namely, (a) its texture is compatible with the existing tissue at the site, (b) it is non-toxic, (c) it is non-reactive (ie, it has low antigenicity), (d) it is stable in the sense that the net amount of tissue remains constant, (e) it is colonized by host cells and is vascularized so that it is resistant to subsequent infection and (f) no immunosuppressive drugs need be administered.

DETAILED DESCRIPTION OF THE INVENTION

The collagen used in the invention method may be collected from any number of mammalian sources. Homograft, autograft and xenograft sources have been used successfully.

The tissue is prepared for treatment by shaving it (if it is animal skin), and removing any loose connective tissue and residual fat. It is then cut into small pieces, dessicated and milled to a powder.

The collagen may be solubilized from the tissue without denaturation (eg, digestion with proteolytic enzymes, salt or acid extraction, or extraction with active amines such as cysteamine and penicillamine) or with denaturation followed by renaturation (eg, heating or treatment with strong acids, detergents or other denaturing chemicals followed by renaturation such as by prolonged incubation at controlled temperatures against acid or neutral low salt neutral solutions). Because the latter procedure is more complex and time-consuming, solubilization without denaturation is preferred, with proteolytic enzyme digestion being particularly preferred.

Many proteolytic enzymes which are not specific collagenases may be used to solubilize collagen without denaturation. For instance, pepsin, trypsin, chymotrypsin or papain may be used. Pepsin is preferred because it is easy to separate from the solubilized collagen. The protease treatment is carried out in an acid medium, pH of 1 to 4.5, and at reduced temperatures in the range of 0° to 15°C.

After solubilization, the solubilized collagen is purified. It has been found that an effective purification of enzyme-solubilized collagen may be made by first separating the enzyme out and then precipitating the collagen sequentially at neutral and acid pH's. An alternative method of purification is the reversible fibril formation technique which involves prolonged dialysis against low ionic strength neutral buffers such as $NaH_2PO_4$ or employing bifunctional anions such as ATP. Further purification of the solubilized collagen by ion exchange chromatography may be carried out if desired.

Following purification the solubilized, native collagen solution is sterilized. Sterilization may be done by dialysis, irradiation, filtration or chemical treatment. The least complicated and most effective of these alternatives is dialysis. An effective sterilization may be made by prolonged dialysis against a weak acid. Weak organic or inorganic acids may be used, with weak alkanoic acids being preferred. Acetic acid is particularly preferred. The sterilized collagen may either be stored as a dilute acid solution or lyophilized and stored in dry, powdered form. It may be stored in either of these forms indefinitely.

The collagen is readied for implantation by reconstituting it into an aqueous solution containing up to 20 mg collagen per ml solution and cooling it to below about 5°C. Preferably the solution contains 12–15 mg collagen per ml solution. A collagen polymerization promoter which causes the solution to be isotonic (pH of about 6–8) is then added. A buffered salt solution which raises the pH to about 7 has been used effectively as a polymerization promoter. Even after the promoter is added the collagen will not polymerize from the solution as long as it is kept chilled. Particles of insoluble collagen microfibrils may be added to the solution to control the shrinkage of the mass formed from the solution at the augmentation site.

The chilled collagen solution with promoter is transferred to an appropriate applicator for implantation, such as a chilled syringe in the case of an injected implant or a chilled container in the case of a surface applique. As soon as the solution is warmed to physiological temperature at the augmentation site polymerization occurs.

When used to augment soft tissue the above described method may be used to treat a large number of congenital anomalies, acquired defects or cosmetic defects. Examples of same are congenital anomalies such as hemifacial microsomia, malar and zygomatic hypoplasia, unilateral mammary hypoplasia, pectus excavatum, pectoralis agenesis (Poland's anomaly), and velopharyngeal incompetence secondary to cleft palate repair or submucous cleft palate (as a retropharyngeal implant); acquired defects (post traumatic, post surgical, post infectious) such as depressed scars, subcutaneous atrophy (eg, secondary to discoid lupis erythematosis), enophthalmos in the enucleated eye (also superior sulcus syndrome), acne pitting of the face, linear scleroderma with subcutaneous atrophy, saddle-nose deformity, Romberg's disease and unilateral vocal cord paralysis; and cosmetic defects such as glabellar frown lines, deep nasolabial creases, circumoral geographical wrinkles, sunken cheeks and mammary hypoplasia.

In non-injection soft tissue augmentation applications the method may be used to fill tissue voids such as the cavity which remains after pituitary ablation or as a sealer to cover skin burns or abrasions. In such latter applications it may be desirable to incorporate suitable drugs in the solution to help prevent secondary infection.

Hard tissue augmentations include cartilage and bone prostheses to promote or effect fusion, restore contour or restore function.

As indicated above, once implanted the collagen quickly polymerizes. Investigations of soft tissue implants in rabbits and rats indicate that after one week the implant is in the form of a white plaque comprising a linear array of loosely arranged, native-type fibrils having a pliant texture. Attempted resolubilization of such implants with nondenaturing solvents has been unsuccessful--indicating the implants are indeed stable. Fibroblast colonization and macroscopic vascularization is in evidence at the one-week stage, and there are abundant blood-filled capillaries. There also appears to be new capillary growth in the form of budding endothelial systems. Colonization and vascularization continue through the second and third weeks after implantation. No gross or microscopic morphologic changes have been observed after the third week.

EXAMPLES

The following examples illustrate the preferred procedure for making the collagen solution which is used in the invention method. These examples are not intended to limit the invention in any manner.

EXAMPLE 1

Source Preparation

Skin was stripped from freshly sacrificed rabbits, shaved, defatted by sharp dissection and cut into one $cm^2$ squares. The skin squares were dessicated in a lyophilizer at ambient temperature for 24 hours and then ground in a Wiley mill to a powder, using solid $CO_2$ to facilitate grinding.

Solubilization

The powdered skin was suspended in 0.5 M acetic acid at 5 g dry wt skin/l. The suspension was cooled to 11°C. A freshly prepared pepsin solution (0.5 g in 10 ml 0.01 N HCl) was added to the skin suspension and the mixture was incubated for 5 days at 11°C with occasional stirring.

Pepsin Removal

Following the solubilization, the pepsin in the mixture was denatured by adding 5 ml Tris base and adjusting the pH to 7.0 with 4 N NaOH at 5°C. 30 g NaCl were stirred into the mixture to keep the collagen in solution. After 4 hours of standing the mixture was centrifuged at 30,000 g for 30 minutes to remove the precipitated pepsin.

Purification

Collagen was precipitated from the supernatant liquid by adding 140 g NaCl with stirring and allowing the liquid to stand for 4 hours at 5°C. The precipitated collagen was centrifuged out at 30,000 g for 30 minutes. The resulting collagen pellet was taken up in 200 ml distilled water and 0.5 N acetic acid was added to make one liter. The collagen was precipitated from this solution by adding 50 g NaCl, allowing the solution to stand for 4 hours at 5°C and centrifuging at 30,000 g for 30 minutes.

Sterilization

The resulting collagen pellet was taken up in 200 ml distilled water, placed in sterilized dialysis tubing and dialysed for 72 hours against 50 volumes 1 N acetic acid. Acetic acid concentration was reduced by then dialysing the solution twice for 24 hours against 50 volumes 0.001 N acetic acid. The solution was then concentrated by placing the dialysis tube on sterile absorbant towels in a laminar-flow bacteriologic barrier until the concentration reached 12–15 mg collagen/ml solution. A known pH was then reestablished by dialysing the concentrate against 50 volumes 0.001 N acetic acid for 24 hours. Following this the concentrate was stored in sterile vials at 5°C pending use.

Addition of Polymerization Promoter to Concentrate

Just prior to use a buffered salt solution, NaCl 2.5 mM/l, NaHPO$_4$ 0.1 mM/l, pH7.4, was added at 5°C to the concentrate in a volume: volume ratio of 1:10 (buffer:collagen), and the buffered concentrate was transferred to a chilled (5°C) syringe.

Use

The above described collagen solution was successfully used as a soft tissue augmentation material in rabbit to rabbit and rabbit to rat implants. The solution polymerized in situ as described above.

EXAMPLE 2

An injectable solution of rat collagen was prepared by the procedure of Example 1 and used successfully as a soft tissue augmentation material in rat to rat implants.

EXAMPLE 3

An injectable solution of human collagen was prepared by the procedure of Example 1 and used successfully as a soft tissue augmentation material in human to rabbit and human to rat implants.

Modifications of the above described invention and the materials and procedures used to make the same which are employed in the invention which are obvious to persons of skill in the biochemical and/or medical arts are intended to be within the scope of the following claims.

We claim:

1. Method of augmenting connective tissue in a living mammal comprising administering a solution of solubilized, purified, native, in situ polymerizable collagen to the mammal at the augmentation site which polymerizes at said site into a fibrous mass of tissue.
2. The method of claim 1 in which the solution is implanted into the mammal by injection.
3. The method of claim 1 in which the solution is administered by coating the augmentation site.
4. The method of claim 1 in which the collagen source is heterologous skin or tendon.
5. The method of claim 1 in which the mammal is a human.
6. The method of claim 1 in which the concentration of collagen in the solution is up to 20 mg/ml.
7. The method of claim 1 in which the concentration of collagen in the solution is about 12 to about 15 mg/ml.
8. The method of claim 1 in which the pH of the solution is about 6 to about 8.
9. The method of claim 1 in which the solution contains a polymerization promoter which causes the solution to be isotonic.
10. The method of claim 9 in which the promoter is a buffered, neutral salt solution.
11. The method of claim 10 in which the buffered, neutral salt solution is a solution of NaCl and NaHPO$_4$, pH 7.4.
12. The method of claim 1 in which the collagen has been solubilized by treatment with a proteolytic enzyme.
13. The method of claim 12 in which the treatment with a proteolytic enzyme is made in an acid medium, pH of 1 to 4.5 at a temperature in the range of 0°C to 15°C.
14. The method of claim 13 in which the temperature is 11°C.
15. The method of claim 14 in which the proteolytic enzyme is pepsin.
16. The method of claim 1 in which the solubilized collagen has been purified by salt precipitation.
17. The method of claim 9 in which the temperature of the solution is kept below about 5°C until it is administered.
18. The method of claim 1 in which particles of insoluble collagen microfibrils are added to the solution before it is administered.
19. The method of claim 1 in which the solution is administered to the skin as a sealer to cover a burn or an abrasion.
20. The method of claim 19 in which the solution contains a drug to prevent secondary infection.
21. The method of claim 1 in which the collagen has been solubilized by treatment with a proteolytic enzyme, the concentration of collagen in the solution is up to 20 mg/ml, the pH of the solution is about 6 to about 8 and the solution contains a polymerization promoter which causes the solution to be isotonic.

* * * * *